US006827708B2

(12) United States Patent
Kirchhofer

(10) Patent No.: US 6,827,708 B2
(45) Date of Patent: Dec. 7, 2004

(54) DEVICE FOR ADMINISTERING AN INJECTABLE PRODUCT IN DOSES

(75) Inventor: Ulrich Kirchhofer, Obergoldbach (CH)

(73) Assignee: Disetronic Services AG, Burgdorf (CH)

( * ) Notice: Subject to any disclaimer, the term of this patent is extended or adjusted under 35 U.S.C. 154(b) by 0 days.

(21) Appl. No.: 10/103,026

(22) Filed: Mar. 21, 2002

(65) Prior Publication Data

US 2002/0099337 A1 Jul. 25, 2002

Related U.S. Application Data

(63) Continuation of application No. PCT/CH00/00475, filed on Sep. 6, 2000.

(30) Foreign Application Priority Data

Sep. 22, 1999 (DE) .......................................... 199 45 397

(51) Int. Cl.[7] ................................................ A61M 5/00
(52) U.S. Cl. ....................................... 604/187; 604/156
(58) Field of Search ................................ 604/134, 131, 604/186, 187, 207, 208, 137, 211, 224, 228, 232, 264, 234, 65, 67, 218, 246, DIG. 12, DIG. 13

(56) References Cited

U.S. PATENT DOCUMENTS 4,781,684 A    11/1988   Trenner ..................... 604/110

FOREIGN PATENT DOCUMENTS

| EP | 0327910 A2 | 8/1989 | ............ A61M/5/24 |
| EP | 0450905 A1 | 10/1991 | .......... A61M/5/315 |
| FR | 2671729 | 7/1992 | ............ A61M/5/24 |
| WO | WO 91/10460 | 7/1991 | ............ A61M/5/24 |
| WO | WO 97/36626 | 10/1997 | .......... A61M/5/315 |

*Primary Examiner*—Manuel Mendez
(74) *Attorney, Agent, or Firm*—Dorsey & Whitney LLP

(57) ABSTRACT

The present invention provides a device for administering an injectable product in doses, wherein the device has a casing with a reservoir for the product, a piston which forces product out of the reservoir when moved in a feed direction towards an outlet of the reservoir, a driven rod which moves the piston in the feed direction, a drive member which may be moved in and counter to the feed direction and which slaves the driven rod when moved in the feed direction, and at least one blocking means for creating friction between said blocking means and one of the driven rod and the casing.

20 Claims, 3 Drawing Sheets

DEVICE FOR ADMINISTERING AN INJECTABLE PRODUCT IN DOSES

PRIORITY CLAIM

This application is a continuation of International Patent Application PCT/CH00/00475, filed on Sep. 6, 2000, which claims priority to an earlier filed German Application Number DE 199 45 397 C2, filed on Sep. 22, 1999.

BACKGROUND OF THE INVENTION

1. Techinical Field

The invention relates to a device for administering an injectable product in doses.

2. Description of the Related Art

A device such as the invention relates to is known for example from WO 97/36626. The device comprises a casing having a reservoir for the product. A piston is accommodated in the reservoir, said piston forcing product out of the reservoir when moved in a feed direction towards an outlet of the reservoir. A gear rack which presses against the piston moves the piston in the feed direction. The gear rack is provided with rows of teeth. A drive member is further accommodated in the casing, shiftable in and counter to the feed direction relative to the casing, said drive member slaving the gear rack when moved in the feed direction. To this end, the drive member meshes with the rows of teeth of the gear rack via slaving means. To set the amount of product administered in one stroke, the drive member in a front position is manually retracted counter to the feed direction by a set dosage path length. In this way, the slaving means of the drive member slide over the teeth of the rows of teeth and give elastically. The gear rack is prevented from moving back by blocking means accommodated unshiftably relative to the casing. The blocking means co-operate with one of the rows of teeth of the gear rack, such that the blocking means prevent the gear rack from moving counter to the feed direction and allow the gear rack to move in the feed direction by elastically giving.

Correctly and precisely dosing the injectable product is of great importance. Above all in medical technology, the success of a treatment is heavily dependent on correctly dosing the medicine. Precise dosing requires a fine pitch of the previously described gear rack, with small teeth. Moreover, the rows of teeth of a gear rack must satisfy the heavy demands of production

SUMMARY OF THE INVENTION

It is the object of the invention to realize a device for administering an injectable product in doses, having simpler components for at least the same functionality.

A device for administering an injectable product in doses comprises a casing having a reservoir for the product, a piston which forces product out of the reservoir when moved in a feed direction towards an outlet of the reservoir, a driven rod which moves the piston in the feed direction, a drive member which may be moved in and counter to the feed direction relative to the casing, said drive member slaving the driven rod when moved in the feed direction, and at least one blocking means which co-operates with the driven rod, such that the blocking means prevents the driven rod from moving counter to the feed direction relative to the casing and allows the driven rod to move in the feed direction.

In accordance with the invention, the driven rod is prevented from moving counter to the feed direction by self-locking. There is a friction lock between the blocking means and the driven rod or a friction lock between the blocking means and the casing. When the driven rod is moved in the feed direction, only the friction lock is overcome. Moving the driven rod counter to the feed direction generates the self-locking of the device via the friction lock, and leads to a friction force which increases with movement of the driven rod counter to the feed direction. A moving force of the driven rod counter to the feed direction thus causes, due to the self-locking of the blocking means, a friction force opposing this moving force which is at least as great. The driven rod can be an easily produced rod made of full material. The use of an internally hollow rod is also possible. A round rod is preferably used. A cornered rod can, however, also be used. The demands of production precision are not heavy. The production costs for such a rod are comparatively low. The term "rod" in the sense of the invention, however, includes in principle any structure extending in the feed direction which is suitable for transmitting the drive force and absorbing the friction force.

If the driven rod is moved in the feed direction, the friction force existing between the blocking means and the driven rod is overcome. Given a preferably unvarying distance between the driven rod and the casing, the blocking means is not tensed further. The force for moving the driven rod in the feed direction remains constantly low. The blocking means does not block the driven rod against relative movement in the feed direction. The driven rod is able to slide past it.

A spring force is preferably used to generate the friction lock between the blocking means and the driven rod or the blocking means and the casing. The spring force can be transmitted via moving parts of the blocking means onto the point of the friction lock, for example by means of a wedge effect via a plane at an angle to the feed direction. One or more annular spiral springs may for example be used, which press one or more tilting elements distributed evenly around the driven rod against the driven rod or the casing. Springs running radially towards the driven rod or the casing at an angle, which generate the friction lock via pressure parts, would also be conceivable.

Particularly preferably, the blocking means comprises at least one spiral spring or leaf spring. When installed, this spring is deflected from its untensed neutral position and is under bending stress. The friction lock is permanently maintained. The spring can consist of metal, plastic or another suitable material or combination of materials. The spring preferably acts directly on the driven rod or the casing. Particularly preferably, the spiral spring or leaf spring form the blocking means alone.

A spring of the blocking means, or the blocking means as such if it is formed by a spring alone, is arranged in the device such that, due to the friction lock, the blocking means is immediately tensed so heavily between the casing and the driven rod when the driven rod is retracted, that in practice it is not possible to noticeably retract the driven rod in the first place. This is preferably achieved by a form and arrangement of the blocking means which are such that a force acting on the blocking means at the point of the friction lock and counter to the feed direction strives to strain the blocking means perpendicularly to the feed direction. If a force is applied to the driven rod counter to the feed direction, a tendency to move together with the driven rod counter to the feed direction into its untensed neutral position is transmitted onto the blocking means via the friction lock. However, it is not possible for the blocking means to simply return to its neutral position, since in its untensed state the blocking means would protrude out from its fixing point across the distance between the casing and the driven rod. A parallel movement of the side of the blocking means abutting the driven rod or the casing could be achieved by shortening the blocking means in its longitudinal direction. However, this is not possible, since a sufficient rigidity of the blocking means against buckling and straining is ensured. In this state, the blocking means clamps between the driven rod and the casing and thus blocks the driven rod against moving counter to the feed direction. In this way, the clamping force forming the friction lock between the blocking means and the driven rod increases superproportionally with a force acting on the driven rod counter to the feed direction. Movement of the driven rod counter to the feed direction is prevented by self-locking.

In a first preferred embodiment, the blocking means is fixed in the casing or at least connected to it unshiftably in the axial direction. To this end, the blocking means is fixed on one side such that movement relative to the fixing, in or counter to the feed direction, is prevented. The blocking means can be stuck on or shrunk on, however it preferably sits in a groove or other recess. It protrudes via another side in a radial direction towards the driven rod. When installed, the blocking means is held on this side in a position deflected in the feed direction by the driven rod. In this way, it is bent around the fixed side, i.e. its fixing absorbs the bending moment. The blocking means is thus under a bending stress, and the resulting elastic restoring force pushes it against the driven rod.

Equally preferably, the blocking means can be attached, axially unshiftable, to the driven rod. The blocking means and the connection between the blocking means and the driven rod can be realized with the same construction as the connection between the blocking means and the casing described above. It protrudes in a radial direction towards the casing and is held in a position deflected counter to the feed direction by the casing. The elastic restoring force thus generated pushes the blocking means against the casing. The blocking principle here corresponds to the blocking principle in a blocking means connected unshiftably to the casing described above. Due to the then altered geometric relations, the kinematic relations run off inversely. To prevent the driven rod from moving counter to the feed direction, the blocking means is therefore deflected counter to the feed direction in this embodiment variant.

Preferably, a smooth surface of the driven rod or of the casing is ensured at least in the area of the friction lock. The blocking means preferably presses against a smooth surface. This is particularly positive for the dosing acuteness of the device. This further improves the ability to dose progressively.

Preferably, at least two springs form each blocking means. They are installed between the casing and the driven rod on opposing sides or, when a number of springs are used, distributed evenly over the circumference of the driven rod. Each of the blocking means is either unshiftably connected to the casing and deflected in the feed direction or unshiftably connected to the driven rod and deflected counter to the feed direction. In this embodiment, the clamping force of the friction lock is evenly distributed over a number of springs. A large clamping force may be achieved. In addition, the springs can form a guide of the driven rod. If only one spring is to be used, then the force can be absorbed in an opposing abutment. The springs are preferably adapted in their form to the respective pressure surface. When unobstructed, the springs preferably protrude radially from the casing or the driven rod. The inner diameter formed by the springs when unobstructed is smaller than that needed by the driven rod or greater than the inner diameter of the casing, respectively. If the driven rod is installed in the casing, the springs are preferably bent around their fixed sides, are simultaneously tensed in the axial direction and press against the driven rod or the casing.

Particularly preferably, the device additionally comprises at least one slaving means which co-operates with the driven rod and the drive member such that when the drive member is moves in the feed direction, the driven rod is slaved by the slaving means, and the slaving means allows the drive member to move counter to the feed direction relative to the driven rod. In accordance with the invention, a friction lock exists between the slaving means and the driven rod or the slaving means and the drive member, said friction lock causing the driven rod to be slaved by self-locking via the drive member. The slaving means works between the drive member and the driven rod in the same way as the blocking means described above. The design and fixing of the slaving means preferably corresponds to that of the described blocking means. Two alternatives again arise. Either the slaving means is unshiftably connected to the drive member and protrudes in a radial direction towards the driven rod and is held in a position deflected in the feed direction by the driven rod, the elastic restoring force of the slaving means thus generated pressing against the driven rod; or alternatively, the slaving means can be unshiftably connected to the driven rod, protrude in a radial direction towards the drive member and be held in a position deflected counter to the feed direction by the drive member, the elastic restoring force of the slaving means thus generated then pressing against the driven means. With respect to the slaving means, all the embodiments of the blocking means apply analogously regarding its arrangement and function.

The slaving means can, however, also be advantageously installed without the blocking means in accordance with the invention, in a device in accordance with claim 10.

BRIEF DESCRIPTION OF THE DRAWINGS

In accordance with the present invention, in some embodiments the slaving means can, however, be advantageously installed without the blocking means.

DETAILED DESCRIPTION

As depicted in the Figures, the injection devices of the present invention may take the form injection pens.

Figures 1, 1A:
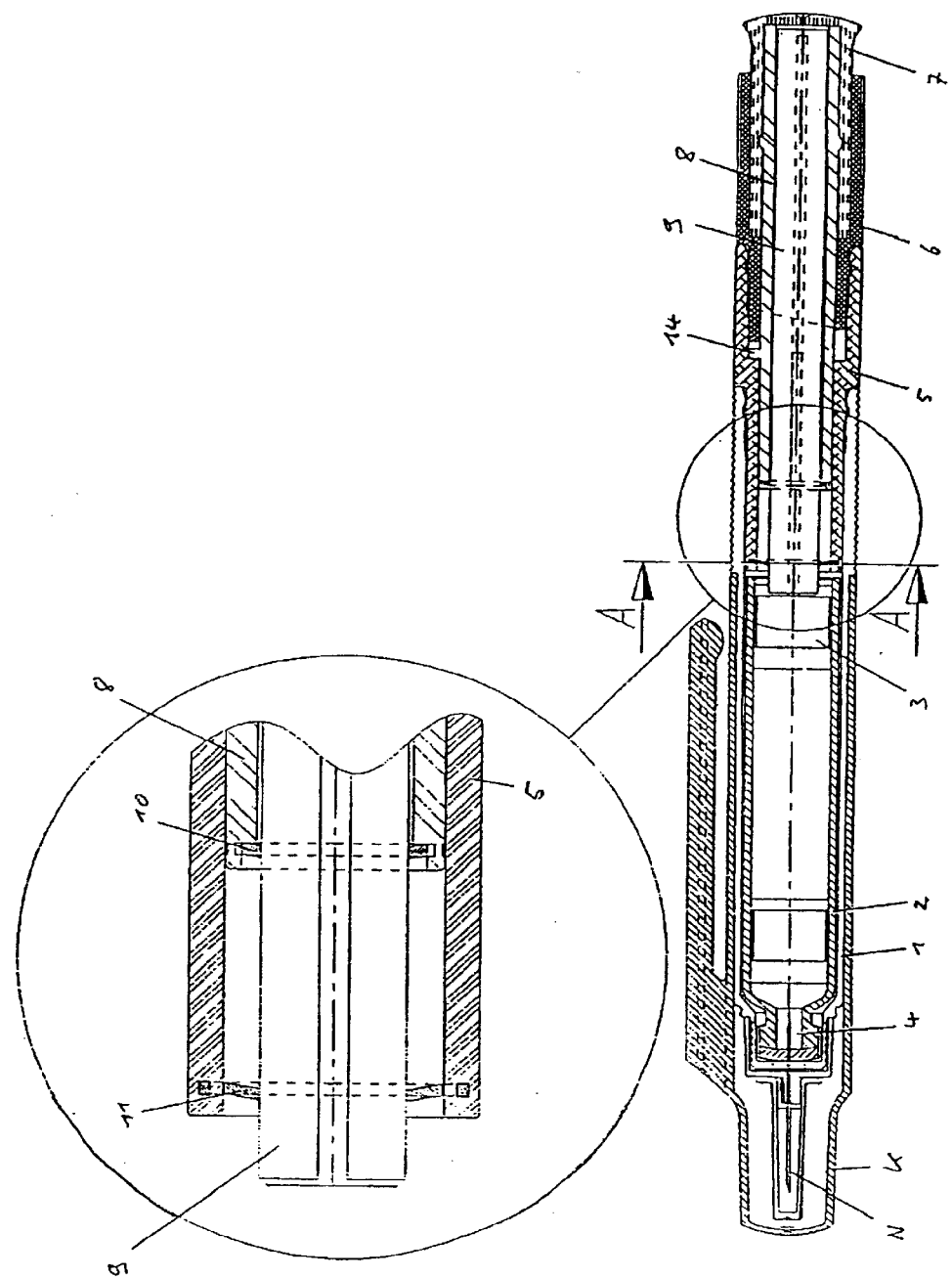
FIG. 1 depicts an embodiment of an injection device in accordance with the present invention.
FIG. 1a is drawn from the circled portion of FIG. 1, and depicts that portion of the embodiment of FIG. 1 is clearer detail.

The injection device in FIG. 1 comprises a casing having a front casing sleeve 1 and a rear casing sleeve 5 securely connected to it. The front casing sleeve 1 serves as a receptacle for an ampoule 2. An injectable product in the form of a liquid active solution, for example insulin, is contained in the ampoule 2. A piston 3 is further accommodated in the ampoule 2. By moving the piston 3 in the feed direction towards an outlet 4 of the ampoule, the product is forced out of the ampoule 2 through its outlet 4, and delivered through an injection needle N. The front casing sleeve 1 is protected by a cap K. The needle N is protected again by a needle cap.

A drive means causes the piston 3 to move in the feed direction, said drive means being accommodated in the rear casing sleeve 5. The drive means comprises a driven rod 9 as the driven member, said driven rod 9 acting directly on the piston 3, and a drive member 8. The drive member 8 is mounted in the rear casing sleeve 5, linearly shiftable in and counter to the feed direction. A lid 7, unshiftably connected to the drive member 8, protrudes rearwards out of the casing.

As in the example embodiment from FIG. 1, the injection pen preferably has a substantially rotationally symmetrical form. It is substantially determined by the form of the casing sleeves 1, 5. The form of the driven rod 9 is independent of this. In the example embodiment, it is realized as a round rod. The driven rod 9 is arranged centrally within the injection pen. The longitudinal axes of the ampoule 2 and the driven rod 9 lie one over the other. The drive member 8 is a substantially cylindrical body, likewise arranged centrally in the injection pen and the casing sleeves 1, 5. The drive member 8 is preferably adapted in its inner side to the outer form of the driven rod, and in its outer side to the inner form of the rear casing sleeve 5.

A dosing member 6, formed as a sleeve body, is connected unshiftably to the rear casing sleeve 5, but rotatable about the common longitudinal axis. The maximum dosage path length which the drive member 8 and the driven rod 9 can cover in the feed direction, and thus also the maximum product dosage which can be delivered in one injection, is adjusted by rotating the dosing member 6. To this end, a front sleeve portion of the dosing member 6 is formed in a circumferential spiral at its front abutting face, i.e. the front sleeve portion progressively falls away from the front section of the abutting face in a circumferential direction, with respect to the longitudinal axis of the injection device. The dosing member 6 can be formed for example in accordance with a dosing member described in WO 97/36625, and can co-operate during dosing with the drive member 8, as described therein.

Dosing takes place at a front position of the drive member 8 with respect to the feed direction, in which a collar and/or cam radially extending from the outer surface area of the drive member 8 abuts a stopper formed by the rear casing sleeve 5. In the front position of the drive member 8, the dosing member 6 is rotated relative to the rear casing sleeve 8 until the desired dosing position is reached. In this dosing position, a slight dosing space remains between a further collar and/or cam likewise radially extending from the outer surface area of the drive member 8 (not shown in the Figure) and the abutting face of the dosing member 6 opposite this cam. The drive member 8 can be retracted by the dosing space relative to the rear casing sleeve 5 and thus also relative to the driven rod 9 and the piston 3 counter to the feed direction. It is manually retracted by pulling on the lid 7. The dosing space is equal to the dosage path length for the subsequent administering.

When the drive member 8 is moved back or retracted, the driven rod 9 remains in its sliding position, assumed during dosage, relative to the casing. It is secured against moving counter to the feed direction by blocking means 11 formed on the rear casing sleeve 5. A friction lock exists between the blocking means 11 and the driven rod 9, said friction lock preventing the driven rod 9 from moving counter to the feed direction by self-locking. The blocking means 11 acts on the driven rod 9 by means of a spring force. In the example embodiment, the blocking means 11 is formed by two plate- or pin-shaped springs 11' connected to each other. The blocking means 11 is connected to the rear casing sleeve 5, axially unshiftable. It is likewise fixed by the rear casing sleeve 5 in a direction perpendicular to the sliding direction. When assembling the injection device, the driven rod 9 is introduced into the rear casing sleeve 5 in such a way that the springs 11' of the blocking means 11 are deflected in the feed direction. The elastic restoring forces of the blocking means 11 thus generated press it against the driven rod 9. If the driven rod 9 is moved counter to the feed direction, the blocking means 11 clamps between the rear casing sleeve 5 and the driven rod 9. With increasing force on the driven rod 9 counter to the feed direction, the friction force increases, and thus the force of the friction lock between the blocking means 11 and the driven rod 9. Movement counter to the feed direction is prevented by self-locking. When the driven rod 9 is moved in the feed direction, the direction of the relative movement between the driven rod 9 and the blocking means 11 matches the deflected direction of the blocking means 11. The driven rod 9 slides in the direction of the bent blocking element 11. The blocking means 11 allows the driven rod 9 to move in the feed direction.

A slaving means 10 is unshiftably connected to the drive member 8. In the example embodiment, it is likewise formed by two plate- or pin-shaped spiral springs connected to each other and deflected in the feed direction. The slaving means 10 works according to the same functional principle as the previously described blocking means 11. In order to adjust the dosage amount, the slaving means 10 allows the drive member 8 to move counter to the feed direction and relative to the driven rod 9. The driven rod 9 is here held in its position by the blocking means 11. To inject the product, the drive member 8 is moved in the feed direction by external pressure on the lid 7. In this sliding direction, the slaving means 10 clamps between the drive member 8 and the driven rod 9. The driven rod 9 is slaved by the slaving means 10 and slides through the blocking means 11 in the feed direction.

The slaving means 10 and/or the blocking means 11 can instead also be unshiftably connected to the driven rod 9, respectively. This does not alter the functionality in principle of the blocking means 11 or slaving means 10, respectively. In order to achieve the same operation as in the previously described embodiment, the slaving means 10 and/or blocking means 11 must be deflected counter to the feed direction when assembling the injection device.

The supporting surfaces against which the slaving means 10 and/or blocking means 11 press are preferably smooth surfaces. Particularly preferably, the slaving means 10 and the blocking means 11 respectively are not fixed in the driven rod 9, and a driven rod 9 is used which is smooth over its whole length or at least in the effective area of the slaving means 10 and the blocking means 11. The driven rod 9 can exhibit a round or cornered cross-section. A round cross-section is preferably used.

Figure 2:
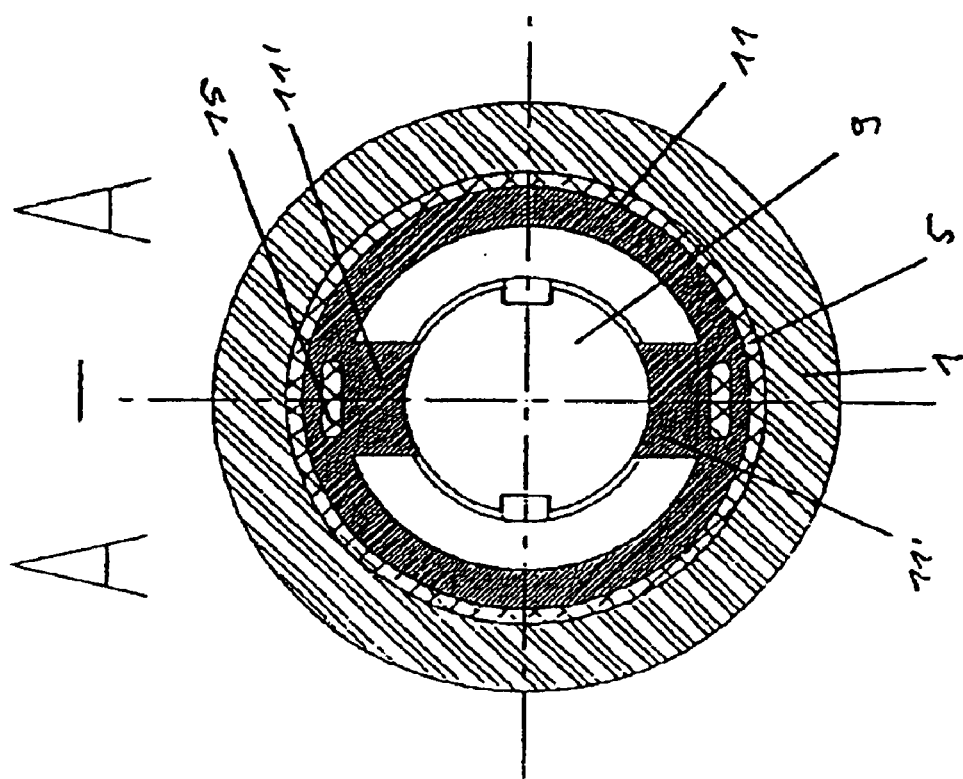
FIG. 2 is a sectional view taken along A—A of FIG. 1.

FIG. 2 shows the cross-section A—A through the blocking means 11. The design also applies analogously to the slaving means 10. In the preferred embodiment, two spiral spring plates 11' are arranged at the same height on opposite sides of the driven rod 9. One spiral spring plate 11' thus forms the abutment for the other spiral spring plate 11', and vice versa. They are fixed, axially unshiftable, in the rear casing sleeve 5. The spring plates 11' protrude radially from the rear casing sleeve 5 towards the driven rod 9, bridging the intermediate space between the rear casing sleeve 5 and the driven rod 9. The sides of the spring plates 11' abutting the driven rod 9 are adapted to the round form of the driven rod 9. The spring plates 11' evenly abut a circumferential area of the driven rod 9. The blocking element 11 forms a supporting ring from which the spring plates 11' radially protrude inwards. The blocking element 11 sits in a receptacle groove circumferentially worked out of the inner surface area of the rear casing sleeve 5. In the initial state of the device, i.e. before the first administering, the blocking element 11 presses against a front area of the driven rod 9. When unobstructed, the distance between the ends of the spring plates 11' protruding freely towards one another is smaller than the outer diameter of the driven rod 9. When assembled, the driven rod 9 bends the spring plates 11' away from each other at their free ends, around the fixed ends in the rear casing sleeve 5. The elastic restoring force of the spring plates 11' forms a friction lock between the rear casing sleeve 5 and the driven rod 9. A sufficiently large bending arm is ensured for the spring plates 11'. The driven rod 9 is preferably non-rotatable. The blocking means 11 is radially secured in particular against coming out of the receptacle groove by a peg 15 which engages with a recess of the blocking means 11. In the case of self-locking, it is important to prevent the individual spiral spring plates from radially slipping outwards. This is achieved on the one hand by the annular connection and on the other hand by the casing wall abutting the outer edge of the spiral spring plates 11'.

Once the rear casing sleeve 5 is produced, the blocking member 11 can be inserted into it. The blocking means 11 is preferably integrated into the rear casing sleeve 5 even during its production process. The rear casing sleeve 5 can for example be produced around the blocking means 11 by injection molding. The spring plates 11' are produced from an elastic material having a sufficiently high friction coefficient, for example of plastic or spring steel. The spring plates 11' and the annular connections preferably consist of one part.

It is easy to recognize how the design of the blocking element 11 is altered if the blocking element 11 is fixed to the driven rod 9 instead of to the casing and pressed against the rear casing sleeve 5. The annular connection which the spring plates 11' abut is then on the inside, and the spring plates 11' radially protrude outwards.

Figures 3, 3A:
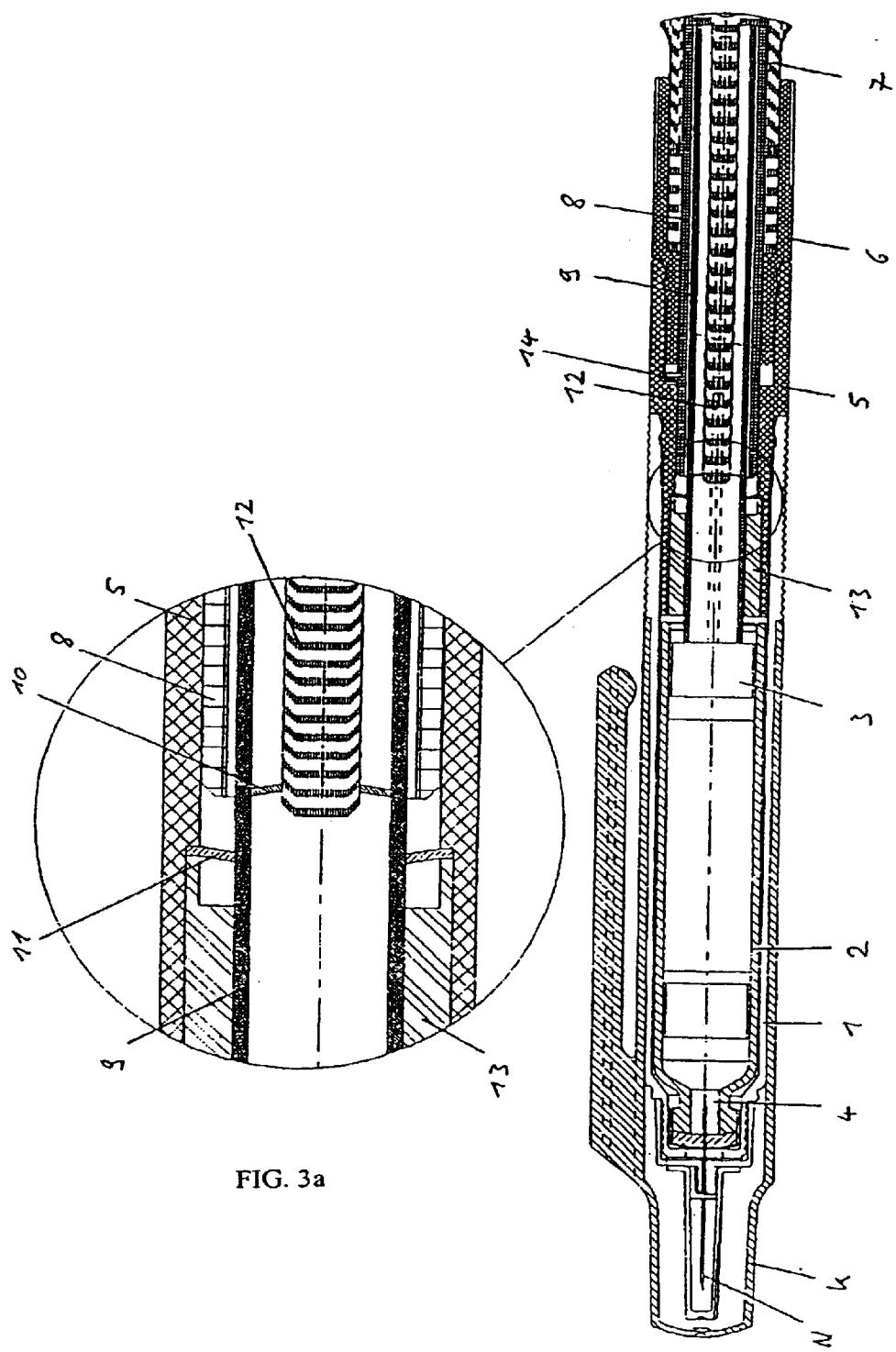
FIG. 3 depicts another embodiment of an injection device in accordance with the present invention.
FIG. 3a is drawn from the circled portion of FIG. 3, and depicts that portion of the embodiment of FIG. 3 is clearer detail.

FIG. 3 shows an injection pen in a second example embodiment using a hollow driven rod 9. The design in principle, and the functionality, correspond to the first example embodiment according to FIG. 1, such that primarily only the differences will be described.

The blocking means 11 is fixed, axially unshiftable, in the rear casing sleeve 5, and again presses towards the driven rod 9 from without. The blocking means 11 sits on a heel of the rear casing sleeve 5 radially protruding inwards, and is pressed against this heel from the other side by means of a supporting sleeve 13 and thus connected, axially unshiftable, to the casing 1, 5. The supporting sleeve 13 is pressed, screwed or simply pushed into the rear casing sleeve 5 and immobilized relative to the rear casing sleeve 5. This principle enables the blocking element 11 to be easily assembled, and can preferably also be used in the example embodiment of FIG. 1. The supporting sleeve 13 fixes the blocking means 11 on the one hand and on the other guides the driven rod 9.

The driven rod 9 is open at its rear end; in the example embodiment, in its form as a simple tube, it is open at both its ends. A rod-shaped lid extension 12 projecting from the base of the lid 7 protrudes into the driven rod 9 from the rear. The slaving means 10 is fixed near the free end of the lid extension 12. The lid extension 12 protrudes at least as far into the driven rod 9 as the piston 3 is to be advanced in the ampoule 2. In the embodiment shown, the slaving means 10 is connected, axially unshiftable, to the lid extension 12 and presses against the hollow driven rod 9 from within.

The functionality of blocking and slaving the driven rod 9 using the blocking means 11 and slaving means 10 follows in the way described in the first example embodiment. Fixing the slaving means 10 or blocking means 11 respectively to the driven rod and/or the casing or drive member respectively can be realized analogously to how it was described above.

The lid extension 12 protrudes through from the base of the sleeve-shaped lid 7 out of the lid 7 and sticks out from the edge of the lid 7 at a certain distance. The sleeve-shaped part of the lid 7 does not impede assembling the slaving means 10 on the lid extension 12. A simple assembly of the slaving means 10 is enabled.

In the foregoing description preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A device for administering an injectable product in doses, comprising:
   a) a casing having a reservoir for the product;
   b) a piston which forces product out of the reservoir when moved in a feed direction towards an outlet of the reservoir;
   c) a driven rod which moves the piston in the feed direction;
   d) a drive member which may be moved in and counter to the feed direction relative to the casing and which slaves the driven rod when moved in the feed direction; and
   e) at least one blocking means which co-operates with the driven rod and the casing, such that the blocking means prevents the driven rod from moving counter to the feed direction relative to the casing and allows the driven rod to move in the feed direction, wherein
   f) a friction lock exists between the blocking means and one of the driven rod and the casing, said friction lock preventing the driven rod from moving counter to the feed direction by self-locking.

2. The device as set forth in claim 1, wherein the blocking means generates the friction lock by means of a spring force.

3. The device as set forth in claim 1, wherein the blocking means comprises at least one spring.

4. The device as set forth in claim 1, wherein the blocking means is unshiftably connected to the casing, protrudes in a radial direction towards the driven rod and is held in a position deflected in the feed direction by the driven rod, the elastic restoring force thus generated pressing the blocking means against the driven rod.

5. The device as set forth in claim 1, wherein the blocking means is unshiftably connected to the driven rod, protrudes in a radial direction towards the casing and is held in a position deflected counter to the feed direction by the casing, the elastic restoring force thus generated pressing the blocking means against the casing.

6. The device as set forth in claim 1, wherein the blocking means presses against a smooth surface of one of the driven rod and the casing in the area of the friction lock.

7. The device as set forth in claim 1, wherein the blocking means comprises at least two plate-shaped springs.

8. A device for administering an injectable product in doses, comprising:
   a) a casing having a reservoir for the product;
   b) a piston which forces product out of the reservoir when moved in a feed direction towards an outlet of the reservoir;
   c) a driven rod which moves the piston in the feed direction;
   d) a drive member which may be moved in and counter to the feed direction relative to the casing;
   e) at least one slaving means which co-operates with the driven rod and the drive member, such that the driven rod is slaved when the drive member moves in the feed direction and the slaving means allows the drive member to move counter to the feed direction and relative to the driven rod; and
   f) a blocking means which co-operates with the driven rod and the casing, such that it prevents the driven rod from moving counter to the feed direction relative to the casing and allows the driven rod to move in the feed direction, wherein
   g) a friction lock exists between the slaving means and one of the driven rod and the drive member, said friction lock causing the driven rod to be slaved by self-locking via the drive member.

9. The device as set forth in claim 8, wherein the slaving means is unshiftably connected to the drive member, protrudes in a radial direction towards the driven rod and is held in a position deflected in the feed direction by the driven rod, the elastic restoring force thus generated pressing the slaving means against the driven rod.

10. The device as set forth in claim 8, wherein the slaving means is unshiftably connected to the driven rod, protrudes in a radial direction towards the drive member and is held in a position deflected counter to the feed direction by the drive member, the elastic restoring force thus generated pressing the slaving means against the drive member.

11. The device as set forth in claim 8, wherein the blocking means comprises two plate-shaped springs that are generally opposite each other.

12. The device as set forth in claim 8, wherein the blocking means comprises two springs that are fixed to generally opposite sides of the driven rod.

13. A device for administering an injectable product in doses, comprising:
   a) a casing having a reservoir for the product;
   b) a piston which forces product out of the reservoir when moved in a feed direction towards an outlet of the reservoir;
   c) a driven rod which moves the piston in the feed direction;
   d) a drive member which may be moved in and counter to the feed direction and which slaves the driven rod when moved in the feed direction; and
   e) at least one blocking means which co-operates with the driven rod and the casing for creating friction between said blocking means and one of the driven rod and the casing.

14. The device according to claim 13, wherein the blocking means co-operates with the driven rod and the casing to prevent the driven rod from moving counter to the feed direction and to allow the driven rod to move in the feed direction.

15. The device according to claim 14, wherein the friction makes the driven rod self-locking against moving counter to the feed direction.

16. A device for administering an injectable product in doses, comprising:
   a) a casing having a reservoir for the product;
   b) a piston which forces product out of the reservoir when moved in a feed direction towards an outlet of the reservoir;
   c) a driven rod which moves the piston in the feed direction;
   d) a drive member which may be moved in and counter to the feed direction relative to the casing and which slaves the driven rod when moved in the feed direction; and
   e) at least one blocking means which co-operates with the driven rod and the casing, such that the blocking means prevents the driven rod from moving counter to the feed direction relative to the casing and allows the driven rod to move in the feed direction, the blocking means being unshiftably connected to the casing, protruding in a radial direction towards the driven rod and being held in a position deflected in the feed direction by the driven rod, the elastic restoring force thus generated pressing the blocking means against the driven rod, wherein
   f) a friction lock exists between the blocking means and one of the driven rod and the casing, said friction lock preventing the driven rod from moving counter to the feed direction by self-locking.

17. A device for administering an injectable product in doses, comprising:
   a) a casing having a reservoir for the product;
   b) a piston which forces product out of the reservoir when moved in a feed direction towards an outlet of the reservoir;
   c) a driven rod which moves the piston in the feed direction;
   d) a drive member which may be moved in and counter to the feed direction relative to the casing and which slaves the driven rod when moved in the feed direction; and
   e) at least one blocking means which co-operates with the driven rod and the casing, such that the blocking means prevents the driven rod from moving counter to the feed direction relative to the casing and allows the driven rod to move in the feed direction, the blocking means being unshiftably connected to the driven rod, protruding in a radial direction towards the casing and being held in a position deflected counter to the feed direction by the casing, the elastic restoring force thus generated pressing the blocking means against the casing, wherein
   f) a friction lock exists between the blocking means and one of the driven rod and the casing, said friction lock preventing the driven rod from moving counter to the feed direction by self-locking.

18. A device for administering an injectable product in doses, comprising:
   a) a casing having a reservoir for the product;

b) a piston which forces product out of the reservoir when moved in a feed direction towards an outlet of the reservoir;

c) a driven rod which moves the piston in the feed direction;

d) a drive member which may be moved in and counter to the feed direction relative to the casing;

e) at least one slaving means which co-operates with the driven rod and the drive member, such that the driven rod is slaved when the drive member moves in the feed direction and the slaving means allows the drive member to move counter to the feed direction and relative to the driven rod, the slaving means being unshiftably connected to the driven rod, protruding in a radial direction towards the drive member and being held in a position deflected counter to the feed direction by the drive member, the elastic restoring force thus generated pressing the slaving means against the drive member; and f) a blocking means which co-operates with the driven rod and the casing, such that it prevents the driven rod from moving counter to the feed direction relative to the casing and allows the driven rod to move in the feed direction, wherein g) a friction lock exists between the slaving means and one of the driven rod and the drive member, said friction lock causing the driven rod to be slaved by self-locking via the drive member.

19. A device for administering an injectable product in doses, comprising:

a) a casing having a reservoir for the product;

b) a piston which forces product out of the reservoir when moved in a feed direction towards an outlet of the reservoir;

c) a driven rod which moves the piston in the feed direction;

d) a drive member which may be moved in and counter to the feed direction relative to the casing;

e) at least one slaving means which co-operates with the driven rod and the drive member, such that the driven rod is slaved when the drive member moves in the feed direction and the slaving means allows the drive member to move counter to the feed direction and relative to the driven rod; and f) a blocking means which co-operates with the driven rod and the casing, such that it prevents the driven rod from moving counter to the feed direction relative to the casing and allows the driven rod to move in the feed direction, the blocking means comprising at least two plate-shaped springs that are generally opposite each other, wherein g) a friction lock exists between the slaving means and one of the driven rod and the drive member, said friction lock causing the driven rod to be slaved by self-locking via the drive member.

20. A device for administering an injectable product in doses, comprising:

a) a casing having a reservoir for the product;

b) a piston which forces product out of the reservoir when moved in a feed direction towards an outlet of the reservoir;

c) a driven rod which moves the piston in the feed direction;

d) a drive member which may be moved in and counter to the feed direction relative to the casing;

e) at least one slaving means which co-operates with the driven rod and the drive member, such that the driven rod is slaved when the drive member moves in the feed direction and the slaving means allows the drive member to move counter to the feed direction and relative to the driven rod; and f) a blocking means which co-operates with the driven rod and the casing, such that it prevents the driven rod from moving counter to the feed direction relative to the casing and allows the driven rod to move in the feed direction, the blocking means comprising two springs that are fixed to generally opposite sides of the driven rod, wherein g) a friction lock exists between the slaving means and one of the driven rod and the drive member, said friction lock causing the driven rod to be slaved by self-locking via the drive member.

* * * * *

UNITED STATES PATENT AND TRADEMARK OFFICE
CERTIFICATE OF CORRECTION

PATENT NO.     : 6,827,708 B2
DATED          : December 7, 2004
INVENTOR(S)    : Ulrich Kirchhofer It is certified that error appears in the above-identified patent and that said Letters Patent is hereby corrected as shown below:

Column 5,
Lines 12 and 16, please delete "example embodiment" and insert -- exemplary embodiment --
Line 67, please delete "example" and insert -- exemplary --

Column 6,
Line 25, please delete "example embodiment" and insert -- exemplary embodiment --

Column 7,
Lines 43, 59 and 63, please delete "example" and insert -- exemplary --
Line 46, please delete "example embodiment" and insert -- exemplary embodiment --

Column 8,
Line 8, please delete "example embodiment" and insert -- exemplary embodiment --

Signed and Sealed this

Fifth Day of April, 2005

JON W. DUDAS
*Director of the United States Patent and Trademark Office*